(12) United States Patent
Schenkl et al.

(10) Patent No.: US 9,861,248 B2
(45) Date of Patent: Jan. 9, 2018

(54) OPTICAL SENSOR FOR WATER-AIR DETECTION

(71) Applicant: emz-Hanauer GmbH & Co. KGaA, Nabburg (DE)

(72) Inventors: Johann Schenkl, Bodenwoehr (DE); Manfredi Signorino, Milan (IT); Johannes Baumer, Fuchsberg (DE); Georg Wilhelm, Guteneck (DE)

(73) Assignee: emz-Hanauer GmbH & Co. KGaA (DE)

( * ) Notice: Subject to any disclaimer, the term of this patent is extended or adjusted under 35 U.S.C. 154(b) by 213 days.

(21) Appl. No.: 14/609,551

(22) Filed: Jan. 30, 2015

(65) Prior Publication Data
US 2016/0223460 A1    Aug. 4, 2016

(51) Int. Cl.
| | | |
|---|---|---|
| *G01N 21/552* | (2014.01) | |
| *A47L 15/00* | (2006.01) | |
| *G01N 21/43* | (2006.01) | |
| *G01N 21/53* | (2006.01) | |

(52) U.S. Cl.
CPC .......... *A47L 15/0018* (2013.01); *G01N 21/43* (2013.01); *G01N 21/552* (2013.01); *A47L 2401/09* (2013.01); *D06F 2202/085* (2013.01); *G01N 21/534* (2013.01); *G01N 2201/08* (2013.01)

(58) Field of Classification Search
CPC ............. G01N 21/49; G01N 2201/062; G01N 2201/08; A47L 5/0018
See application file for complete search history.

(56) References Cited

U.S. PATENT DOCUMENTS

| | | |
|---|---|---|
| 4,733,335 A | 3/1988 | Serizawa et al. |
| 4,994,682 A | 2/1991 | Woodside |
| 5,140,842 A | 8/1992 | Kiuchi et al. |

(Continued)

FOREIGN PATENT DOCUMENTS

| | | |
|---|---|---|
| DE | 102007053558 A1 | 5/2009 |
| JP | 59-192921 A | 11/1984 |

(Continued)

OTHER PUBLICATIONS

Office action from Polish Patent Office to co-pending application P-415536, dated Oct. 4, 2016.

(Continued)

*Primary Examiner* — Tony Ko
(74) *Attorney, Agent, or Firm* — Robert R. Deleault, Esq.; Mesmer & Deleault, PLLC

(57) ABSTRACT

A sensor and a method of manufacture of a sensor includes a light interface portion comprising first and second walls, where a cavity is provided between the first and second walls, and where the first wall is configured such that at least a portion of light is totally reflected at the first wall when the sensor-external medium is water, and at least a portion of light is coupled out when the sensor-external medium is air, and a portion of light is coupled out and a further portion of light is totally reflected by the first wall when the sensor-external medium comprises foam. Light that is reflected by the first wall is directed toward a second wall, and reflected at the second wall to be directed to a light receiving element.

18 Claims, 3 Drawing Sheets

(56) References Cited

U.S. PATENT DOCUMENTS

| | | | |
|---|---|---|---|
| 5,704,704 A * | 1/1998 | Reichard | B63B 45/04 |
| | | | 362/267 |
| 5,947,587 A | 9/1999 | Keuper et al. | |
| 6,561,690 B2 | 5/2003 | Balestriero et al. | |
| 6,599,002 B2 | 7/2003 | Hsieh et al. | |
| 6,924,943 B2 | 8/2005 | Minano et al. | |
| 7,559,672 B1 | 7/2009 | Parkyn et al. | |
| 7,909,494 B2 | 3/2011 | Chung et al. | |
| 8,648,321 B2 * | 2/2014 | Schenkel | A47L 15/4297 |
| | | | 250/227.11 |
| 2007/0274084 A1 | 11/2007 | Kan et al. | |
| 2009/0116243 A1 | 5/2009 | Condon et al. | |
| 2012/0120667 A1 | 5/2012 | Schenkl | |

FOREIGN PATENT DOCUMENTS

| | | |
|---|---|---|
| JP | 62-204143 A | 9/1987 |
| JP | 02-105020 A | 4/1990 |
| PL | 204205 B1 | 12/2009 |

OTHER PUBLICATIONS

Polish Patent Office Search Report in co-pending application P-415536, dated Jun. 23, 2016.

* cited by examiner

FIG 5  N-N (4:1)
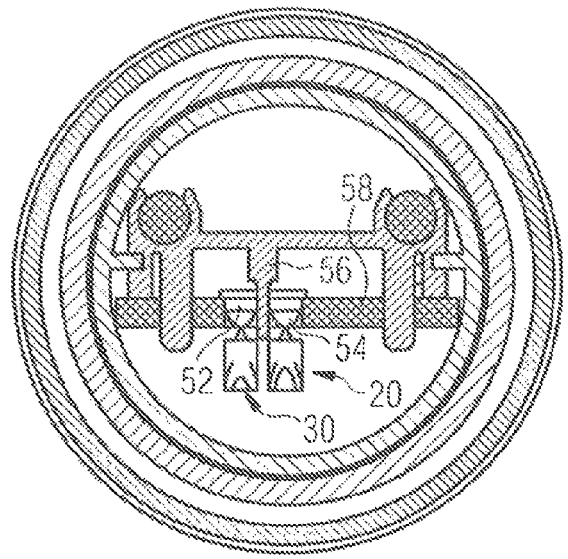
FIG 6
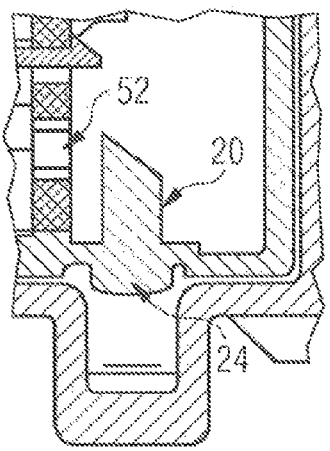
FIG 7
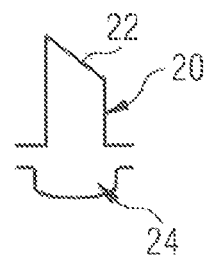

OPTICAL SENSOR FOR WATER-AIR DETECTION

BACKGROUND OF THE INVENTION

1. Field of the Invention

The present invention relates generally to the detection of air and water and, at least in certain embodiments, foam in a medium external to an optical sensor. Particularly, the sensor is configured for use in a washing machine, a dishwasher, or another environment in which it is desired to detect a presence of water, air, or foam in an environment.

2. Description of the Prior Art

Existing sensors for detecting a presence of water, air, or foam may suffer from the drawback that they may be expensive to produce, or may have a complicated internal structure. Some known sensors are configured such that a light source and a light sensor are positioned on a rear side of a lens to sense a composition of a medium external to the lens. Such sensors suffer from the drawbacks that the pieces of the sensors are expensive to produce, and the individual components of the sensors are difficult to assemble.

Additionally, sensors for detecting a present of water, air, or foam may have the disadvantage of being susceptible to becoming encrusted with deposits on a sensing surface, which may cause the sensor to provide inaccurate readings.

Therefore, what is needed is a water-air-foam detector that can provide accurate results and be manufactured economically.

SUMMARY OF THE INVENTION

It is an object of the present invention to provide a water-air-foam detector that can provide accurate results and be manufactured economically.

It is another object of the present invention to provide a sensor that can provide excellent sensing of water and air and, in certain embodiments, foam in a medium, and which is easy and inexpensive to produce. A method of manufacturing such a sensor is also provided.

The present invention achieves these and other objectives by providing, in one configuration of an optical sensor of the present invention, an optical sensor comprising a housing having a housing interior and a light interface portion, a light emitting element disposed in the housing interior, a light receiving element disposed in the housing interior, the light interface portion protruding from a base portion of the housing and comprising a first wall disposed to receive light emitted by the light emitting element, a second wall disposed such that light reflected from the second wall is received by the light receiving element, and a cavity formed between the first and second walls, where each of the first and second walls comprises a wall inner surface and a wall outer surface, where the outer surface of the first wall defines an optical interface between a material of the wall and a sensor-external medium and is configured such that, when the sensor-external medium is air, at least a portion of the light emitted by the light emitting element is totally reflected at the outer surface of the first wall and is directed from the first wall through the cavity to the second wall and from the second wall to the light receiving element, and when the sensor-external medium is water, at least a portion of the light emitted by the light emitting element is coupled out into the sensor-external medium at the outer surface of the first wall.

In certain embodiments, the first and second walls are disposed at an angle with respect to each other. The angle between the first and second walls may be within a range from 60 to 120 degrees or 70 to 110 degrees or 80 to 100 degrees and may, in certain embodiments, be approximately 90 degrees.

In certain embodiments, the wall inner surface of at least one of the first and second walls has a stepped formation. A height and/or width of steps of the stepped formation may have a dimension that is within a range of approximately 0.5 to 1.0 millimeters.

In certain embodiments, the optical sensor further comprises first and second light guides accommodated in the housing, wherein the first light guide is disposed to direct light from the light emitting element toward the first wall, and the second light guide is disposed to direct light from the second wall to the light receiving element. The first and second light guides may be disposed adjacent to the cavity formed between the first and second walls and they may extend in parallel with each other. More specifically, the first and second light guides may extend substantially parallel to a printed circuit board carrying the light emitting element and the light receiving element.

In certain embodiments, at least one of the first and second light guides comprises a converging lens at an end thereof proximal to the cavity.

In certain embodiments, at least one of the first and second light guides has an angled or curved, for example, convex surface portion at an end thereof remote from the cavity to direct light to a light output port of the respective light guide by total reflection.

In certain embodiments, the light emitting element and the light receiving element are disposed on a printed circuit board, the light emitting element has a main emission axis substantially perpendicular to the printed circuit board, and the light receiving element has a main reception axis substantially perpendicular to the printed circuit board. The first light guide is configured to divert a light ray emitted from the light emitting element in the direction of the main emission axis to a direction substantially parallel to the printed circuit board, and the second light guide is configured to divert a light ray travelling in the second light guide parallel to the printed circuit board to a direction substantially parallel to the main reception axis.

In certain embodiments, the first and second light guides are provided on a light guide support that has a portion configured to conform to at least a portion of an inner surface of the base portion of the housing. The light guide support may further comprise a substantially cylindrical portion configured to conform to an inner surface of a substantially cylindrical portion of the sensor housing.

In certain embodiments, a ratio of the amount of light received by the light receiving element to the light emitted by the light emitting element is: less than 20% when the sensor-external medium is water, more than 80% when the sensor-external medium is air, and between 20% and 80% when the sensor-external medium comprises foam.

In certain embodiments, a material of the first and second walls includes polypropylene, and a material of a transparent light guide structure accommodated in the housing to guide light travelling from the light emitting element to the light receiving element includes a transparent material consisting of, e.g., polycarbonate or PMMA (polymethylmethacrylate) or polyamide.

In certain embodiments, the wall outer surface of at least one of the first and second walls is planar.

In another aspect, there is provided an electric home appliance comprising: a cabinet including a wet compartment for receiving items to be washed; an optical sensor including a light emitting element and a light receiving element; and a control unit configured to receive a measurement signal based on light received by the light receiving element and control an operation of the appliance based on the measurement signal. wherein the optical sensor comprises: a housing having a housing interior and a light interface portion, the light emitting element and the light receiving element disposed in the housing interior, the light interface portion protruding from a base portion of the housing, the light interface portion comprising a first wall disposed to receive light emitted by the light emitting element, a second wall disposed such that light reflected from the second wall is received by the light receiving element, and a cavity formed between the first and second walls, wherein each of the first and second walls comprises a wall inner surface and a wall outer surface, wherein the outer surface of the first wall defines an optical interface between a material of the wall and a sensor-external medium and is configured such that, when the sensor-external medium is air, at least a portion of the light emitted by the light emitting element is totally reflected at the outer surface of the first wall and is directed from the first wall through the cavity to the second wall and from the second wall to the light receiving element, and when the sensor-external medium is water, at least a portion of the light emitted by the light emitting element is coupled out into the sensor-external medium at the outer surface of the first wall, wherein the optical sensor is mounted in the cabinet to protrude with the first and second walls into the wet compartment.

The home appliance may be a washing machine or a dishwasher, for example.

BRIEF DESCRIPTION OF THE DRAWINGS

FIG. 5 is a cross-sectional view of the sensor along line N-N indicated in FIG. 1.
FIG. 6 is a further detailed view of the light guides and the light emitting portion.
FIG. 7 illustrates a configuration of the light guide.

DETAILED DESCRIPTION

Figure 1:
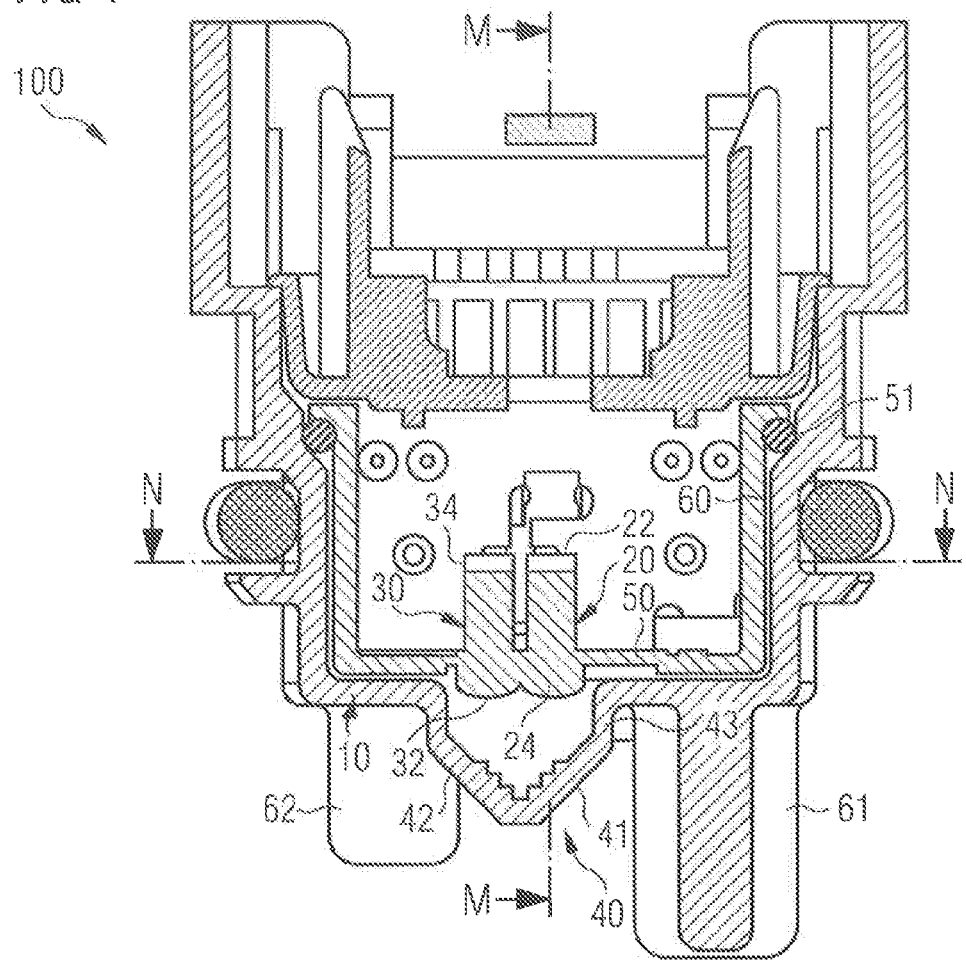
FIG. 1 is a cross-sectional view of the sensor.

FIG. 1 shows a cross-sectional view of the sensor 100. The sensor 100 is configured for use in detecting an amount of water, foam, and/or air in a medium. Examples of specific applications for the sensor are use in a washing machine or a dishwasher.

The sensor 100 comprises a sensor housing 10. The sensor housing 10 may enclose an interior of the sensor, alone or in combination with further components. The sensor housing 10 may be at least partially transparent. The sensor housing 10 may be comprised of a plastic material, e.g., polypropylene. The sensor housing 10 may be manufactured by injection molding. Specifically, the housing 10 is configured to, at at least a portion of a light interface portion 40, allow light to pass therethrough or to be totally internally reflected, depending on a medium located outside the light interface portion 40.

The interior of the sensor 100 comprises a light source 52 and a light receiving element 54. The light source 52 may be an LED (light emitting diode). Alternatively, the light source 52 may be composed of optical fibers, or may comprise an incandescent light source.

A first light guide 20 is provided in the interior of the housing 10, and is configured to guide light therethrough. The first light guide 20 may itself comprise the light source 52, or may be configured to transmit light from the light source 52 provided separately therefrom and configured to emit light into the first light guide 20.

In the configuration of FIG. 1, the light source 52 is configured to emit light toward the first light guide 20. The first light guide 20 comprises a first end 22 opposite a second end 24 at which the light source 52 emits light to the first light guide 20. The second end 24 may comprise a converging lens, such that light that exits the first light guide 20 is collimated. The converging lens may be composed of PMMA or polycarbonate.

The first light guide 20 may comprise an elongated body. The first end portion 22 of the first light guide 20 may comprise an angled upper surface (as seen in FIG. 7), that is angled or curved, and may be specifically a convex surface. This upper surface is configured to divert the light emitted by the light source 52 toward the second end 24 of the first light guide 20 by total reflection. For example, the light emitted by the light source 52 may be reflected so as to enter the converging lens provided at the second end 24 (as illustrated in FIG. 6). As such, the light source 52 may be positioned to emit light toward the angled or curved surface and may be oriented so as to emit light perpendicularly to or at an angle with respect to the direction of light emitted from the second end 24 of the first light guide 20.

As an alternative, the light source 52 may be positioned to emit light toward the converging lens of the second end 24 of the first light guide 20, and the first end 22 of the light guide 20 may receive the light emitted from the light source 52 without reflecting or changing a direction of the light emitted from the light source 52.

The second light guide 30 is configured to guide light received at a first end 32 thereof. The first end 32 may comprise a converging lens. The second light guide 30 further comprises a second end 34, which is configured to guide light to the light receiving element 54. The second end 34 may be configured to reflect light travelling through the second light guide 30 at the angled or curved surface so as to enter the light receiving element 54. The light receiving element 54 may be, therefore, oriented at an angle or perpendicularly with respect to the second light guide 30. The converging lens may be composed of PMMA or polycarbonate.

The light receiving element 54 may be disposed so as to receive light emitted from the second end portion 34 of the second light guide 30. The light receiving element 54 may be, specifically, disposed so as to receive light emitted in a direction perpendicularly to or at an angle with respect to the direction of the light travelling through the second light guide 30 from the first end 32 thereof to the second end 34 thereof. The light receiving element 54 may be configured to receive light reflected at the angled or curved second end 34 toward the light receiving element 54.

As an alternative, the light receiving element 54 may be positioned to receive light from the second light guide 30 without reflection of the light at the second end 34 of the second light guide 30.

Because the first and/or second light guides 20, 30 may comprise the converging lenses, the respective first and/or second light guides 20, 30 may be positioned at a distance from the light interface portion 40. That is, since the directions of the light rays are collimated, the distance of the light guides 20, 30 from the light interface portion 40 does not substantially affect the optical performance of the sensor 100.

The light interface portion 40 may protrude from a surface of the housing 10. The light interface portion 40 comprises at least first and second walls 41, 42. The first and second walls 41, 42 project into a space containing a sensor-external medium, the nature of which is to be detected by means of the sensor (i.e. whether or air or water, for example). The space can be part of a wet compartment designed to receive dirty dishes in the case of a dishwashing machine or laundry in the case of a washing machine. Outer surfaces of the first and second walls 41, 42 may be generally planar. An outer surface of the first wall 41 may define a refractive boundary between the light interface portion 40 and a surrounding medium. Optionally, an outer surface of the second wall 42 may also define a refractive boundary between the light interface portion 40 and the surrounding medium. Inner surfaces of the walls 41, 42 surround a cavity disposed therebetween. The cavity may be filled with air or another generally transparent medium. The first and/or second walls 41, 42 may be at least partially transparent.

The first and second walls 41, 42 may be angled with respect to each other. An angle between inner surfaces of the first and second walls 41, 42 may be within a range of 80 to 100 degrees and is about 90 degrees in the example embodiment shown in the drawings.

The first wall 41 may be positioned opposite the second end portion 24 of the first light guide 20, such that light that exits the second end portion 24 of the first light guide 20 is emitted from the first light guide 20 toward the inner surface of the first wall 41 of the light interface portion 40. For example, a light axis of light that exits the first light guide 20 may have an angle of approximately 15 to 30 degrees, or between 17.5 and 27.5 degrees, or between 20 and 25 degrees, with respect to the outer surface of the first wall 41.

The second wall 42 may be positioned opposite the first end 32 of the second light guide 30, such that light reflected within the cavity formed between the first and second walls 41, 42 may enter the first end 32 of the second light guide 30. The light is collimated by the converging lens provided at the first end 32 of the second light guide and is directed toward the second end 34 of the second light guide 30 and to the light receiving element 54.

Signals output by the light receiving element 54 may be processed to determine a presence or absence of foam, water, and/or air in a medium located external to the sensor housing 10. Specifically, the sensor is configured to detect presence or absence of foam or water in a medium adjacent to the light interface portion 40 of the sensor housing 10.

Inner surfaces of the first wall 41 and optionally the second walls 42 may have a stepped configuration. The steps of the stepped configuration may be within a range of approximately 0.2 and 1.5 millimeters or approximately 0.4 and 1.0 millimeters. For example, the height and/or width of each step may be no less than 0.3 millimeters or no less than 0.4 millimeters or no less than 0.5 millimeters and may be less than 1.3 millimeters or less than 1.1 millimeters or less than 1.0 millimeters.

The stepped configuration is configured to reduce internal reflection within the light interface portion 40 with respect to planar inner surfaces. For example, the steps may be configured such that respective surfaces of the steps are oriented substantially in parallel and/or perpendicular to a light axis of light exiting the first light guide 20, so that the light from the light guide 20 is incident on the outer planar surface of the first wall 41.

Because internal reflection and scatter inside the light interface portion 40 is reduced by the stepped inner surfaces, a thickness of the material of the first and/or second walls 41, 42 can be reduced while still accomplishing the transmission of light from the first light guide 20 to the outer surface of the first wall 41 (and, if internal reflection or scatter occurs, to the second wall 42). A largest thickness of the first and second walls 41, 42 in one embodiment may be less than 2.5 millimeters or less than 2 millimeters or less than 1.5 millimeters or less than 1.2 millimeters or less than 1.0 millimeters (owing to the stepped configuration of the inner surfaces of the walls 41, 42, the wall thickness varies across each step). A smallest thickness of the first and second walls 41, 42 in one embodiment may be no less than 0.8 millimeters or no less than 1.0 millimeters or no less than 1.2 millimeters, in order to achieve sufficient electrical isolation of electrical components accommodated in the sensor housing 10.

The light interface portion 40 may further have a third wall that extends perpendicularly from a base of the sensor to connect the angled first and/or second walls 41, 42 to the base of the sensor housing 10.

The first wall 41 forms a refractive boundary between the medium located externally to the light interface portion 40 of the housing 10 and the material of the first wall 41, so that light incident on the first wall 41 will be either reflected or refracted at the outer surface of the first wall 41, depending on a composition of the medium located outside the first wall 41. Optionally, the second wall 42 may also be configured, like the first wall 41, to reflect or refract light at an outer surface thereof depending on a composition of the medium external thereto. As an alternative, an inner surface of the second wall 42 may be planar and/or reflective, so as to reflect light incident thereon toward the second light guide 30.

The outer surface of the first wall 41 is configured such that, when the external medium consists of air, light incident thereon is substantially reflected. That is, the refractive index of the material of the first wall 41 and/or the angle at which the light from the light guide 20 is incident onto the first wall 41 may be configured such that a critical angle is generated between the first wall 41 and the medium to provide the desired reflection characteristics. The second wall 42 may be configured similarly or identically to the first wall 41.

When the medium consists of air, light from the light source 20 that is directed toward the first wall 41 is internally reflected at the outer surface of the first wall 41 and is directed toward the second wall 42. The second wall 42 reflects the light incident thereon toward the second light guide 30. The second light guide 30 directs the light incident thereon to the light receiving element 54. As such, depending on the portion of the light emitted by the light source 52 that is returned to the light receiving element 54, it can be determined whether the medium consists of air, water, and/or foam. For example, it is possible to configure the light interface portion 40 such that 80-100% of light emitted by the light source 52 is internally reflected when the medium consists of air. When the medium consists of water, at least a portion of the light from the light source 20 that is incident on the first wall 41 is coupled out into the medium, such that no light or only a relatively small portion of light is internally reflected and returned to the light receiving element 54. As such, when no light or a small amount of light is sensed by the light receiving element 54, it can be determined that the medium consists predominantly of water. For example, it is possible to configure the light interface portion 40 such that more than 80% of light emitted by the light source 52 is coupled out when the medium consists of water.

When the medium comprises foam, for example, from a detergent product, the light from the light source 20 that is incident on the light interface portion 40 is partially internally reflected and partially coupled out such that between 20-80% of light is received by the light receiving element 54. Specifically, foam comprises several reflective and absorptive surfaces caused by bubbles of the foam. As such, when an amount of light received by the light receiving element 54 is more than an amount of light received in a case of water and less than an amount received in a case of air, it can be determined that the medium comprises foam. Further, it may be possible to estimate a relative amount of foam in the medium based on the amount of light received by the light receiving element 54.

The above-named values for the amount of internal reflection in the case of air and the amount of coupling out in the case of water may vary. For example, as long as a range exists between these two values which can be assigned to a presence of foam in the medium, the light receiving element 54 may be used to sense the presence of air, water, and foam. Thus, for example, the values for internal reflection in the case of air and coupling out in the case of water may vary largely, so long as the percentage of light that returns to the light receiving element 54 in the cases of water and air is distinguishably different.

Figure 2:
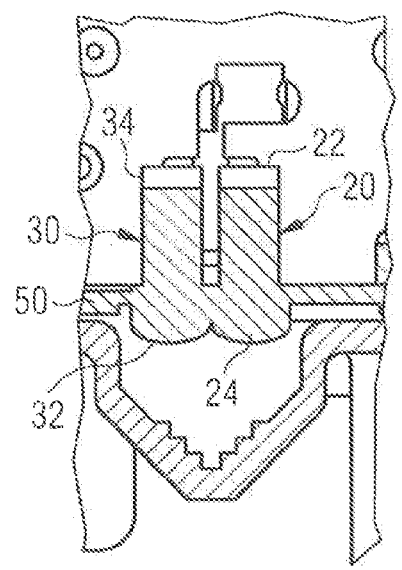
FIG. 2 is a detailed view of the light interface portion.
Figure 3:
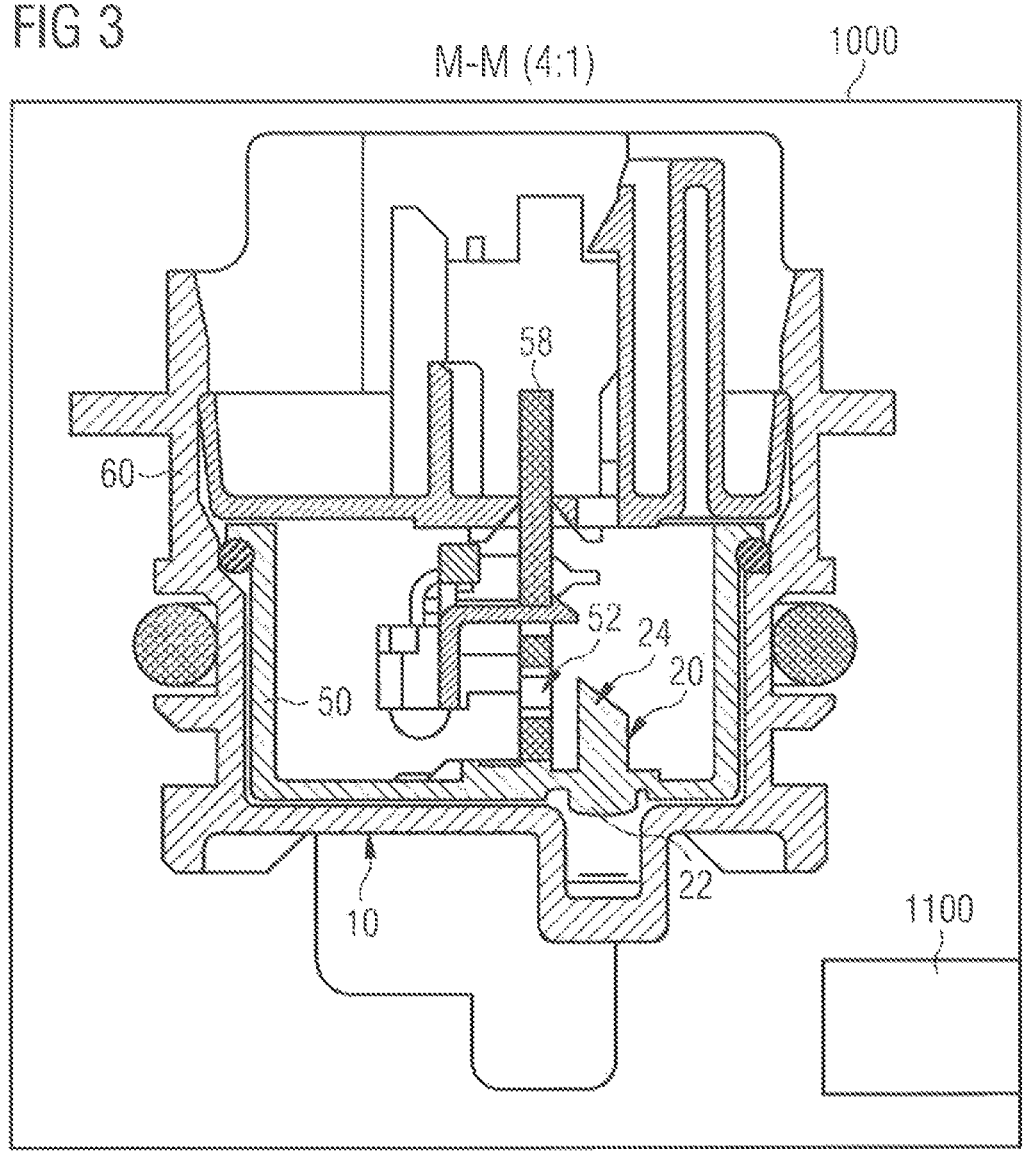
FIG. 3 is a cross-sectional view of the appliance including the sensor along line M-M indicated in FIG. 1.

As illustrated in FIGS. 1 and 2, the light guides 20, 30 may be provided on a light guide support 50. The light guide support 50 may be formed to fit or be installed into a portion of the sensor housing 10 adjacent the light interface portion 40. For instance, the light guide support 50 may be configured to fit into a portion of the sensor housing 10 adjacent the light interface portion 40 such that the second end 24 of the first light guide 20 and the first end 32 of the second light guide 30 are directed toward the light interface portion 40. Remaining portions of the light guide support 50 may correspond to a surrounding surface of a base portion of the sensor housing 10 so that the light guide support 50 may be fastened to or fitted to the sensor housing 10 by inserting the light guide support 50 into the sensor housing 10. Specifically, features that conform to the light guide support 50 to hold the light guide support 50 in a fixed position with respect to the sensor housing 10 may be provided on the sensor housing 10. Further, the light guides 20, 30 may be integrally formed with the light guide support 50, or may be installed into the light guide support 50 before the light guide support 50 is installed into the sensor housing 10. A sealing member 51 (having, e.g., an O-ring design) is interposed between the housing 10 and the light guide support 50 to seal an electronics compartment inside the housing 10 against intrusion of water or another sensor-external medium in the case of damage to a housing portion, e.g., to the light interface portion 40, that is immersed into the medium during operation of the apparatus equipped with the sensor 100. The electronics compartment may accommodate, e.g., a printed circuit board described further below.

The first and second light guides 20, 30 may protrude into the cavity provided between the first and second walls 41, 42, which may reduce an overall size of the sensor. Alternatively, the first and second light guides 20, 30 may be provided at a distance from the cavity provided between the first and second walls 41, 42, such that the configuration and assembly of the sensor 100 is made simple and adaptable.

Figure 4:
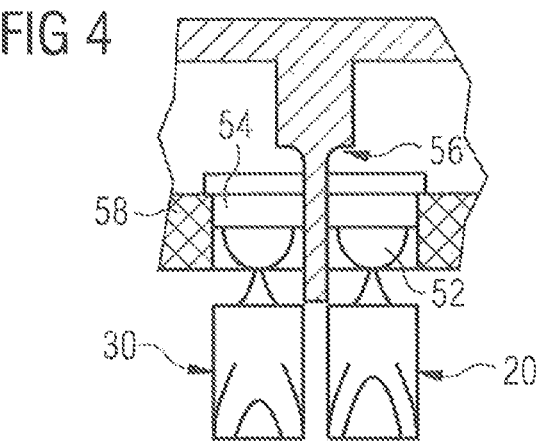
FIG. 4 is a detailed view of the light receiving and light emitting portions and the light guides.

As best illustrated in FIGS. 2, 4, and 5, the light source 52 and the light receiving element 54 may be provided on a printed circuit board (PCB) 58. The PCB 58 may support the light source 52 and the light receiving element 54 thereon, as well as additional electronic components. For example, electric couplings to a power source for powering the light source 52 and electrical connections to connect the light receiving element 54 to a processing means for processing a signal from the light receiving element 54 may be provided on or within the PCB 58. The PCB 58 may comprise coupling features that interact with features of the light guide support 50 and/or the sensor housing 10 such that the alignment of the light source 52 and the light receiving element 54 to the light guides 20, 30 is automatically accomplished upon coupling of the PCB 58 to the light guide support 50 and/or the sensor housing 10.

For example, as illustrated in FIG. 5, portions of the sensor housing 10 and/or the light guide support 50 may be provided that protrude through holes provided in the PCB 58 to position and support the PCB 58 with respect to the light guide support 50.

Further, the PCB 58 may comprise a shield 56 provided between the light source 52 and the light receiving element 54, to prevent light from the light source 52 from being picked up by the light receiving element 54 without passing through the light interface portion 40.

In an alternative embodiment not illustrated in the appended Figures, the first light guide 20 may comprise the light source 52 and the second light guide 30 may comprise the light receiving element 54, which may be directly provided to the light guide support 50. As such, light from the light source 52 and light incident on the light receiving element 54 does not have to be perpendicularly reflected. Also, the first and second light guides 20, 30, may be made smaller in size, if desired, and at least the first light guide 20 may comprise a converging lens.

Since the first light guide 20 may emit collimated light, the first light guide 20 may be disposed at a distance from the inner surface of the first wall 41. As such, the cavity may be provided between the first light guide 20 and the first wall 41. This allows the light interface portion 40 to be protruded into the medium with respect to the sensor housing 10. Further, the first light guide 20 may be provided on the light guide support 50 that is adjacent the base of the sensor housing 10. Thus, the first light guide 20 does not have to be installed protruding into the space between the first and second walls 41, 42. Further, because light reflected from the inner surfaces of the first and second walls 41, 42 enters the converging lens on the first end 32 of the second light guide 30, the second light guide 30 also does not have to be placed protruding into the space between the first and second walls 41, 42. As such, the construction of the sensor can be greatly simplified by placing the light guides 20, 30 on the light guide support 50 and fastening the light guide support 50 to the base of the sensor housing 10.

The light guide support 50 may further comprise sidewalls 60 extending generally perpendicularly to the portion of the light guide support 50 on which the light guides 20, 30 are disposed, which walls may correspond to at least a portion of inner surfaces of the sensor housing 10, such that the light guide support 50 may be installed into the sensor housing 10 by simply inserting the light guide support 50 along the inner surfaces of the sensor housing 10.

Further, providing the PCB 58 comprising the light source 52 and the light receiving element 54 has the advantage that it is possible to integrate many or all electronic features of the sensor 100 onto the sensor support 58, so that electronic features do not have to be separately installed. For example, in order to install the light source 52 and the light receiving element 54 to the light guides 20, 30, the light source 52 and the light receiving element 54 can be preassembled onto the PCB 58, and the PCB 58 needs only to be inserted into the sensor housing 10 such that the light source 52 and the light receiving element 54 are aligned with the respective light guide 20, 30, and further electrical couplings are not necessary. Therefore, the configuration of the present disclosure further provides the advantages that manufacture of the sensor 100 is made easy, as individual positioning and electric or optical connection or alignment of the individual features does not have to be undertaken. Rather, the light source 52 and the light receiving element 54 are already electronically coupled to the PCB 58, and the light guides 20, 30 are preassembled on or integrated with the light guide support 50, and the light guide support 50 and the PCB 58 can be aligned with respect to each other such that the operative portions of the sensor are correctly optically coupled.

The light interface portion 40 may have chemical resistance to a detergent (e.g. a laundry detergent or a dishwasher detergent) while at the same having light transmitting properties. A suitable material of the light interface portion 40 may be polypropylene. An advantage of the present disclosure is that the walls 41, 42 may be made thin, since the desired optical characteristics may be obtained using the previously described stepped inner surface and the planar outer surface of at least the first wall 41 of the light interface portion 40, with the first and second walls 41, 42 provided at an angle with respect to each other, such that undesired internal absorption or attenuation of the light traversing the walls 41, 42 can be reduced. The reduced thickness of the walls 41, 42 reduces the amount of material needed to form the walls 41, 42, and it may also be easier to obtain acceptable transparency levels with thinner walls 41, 42. Therefore, the structure of the present disclosure is less expensive to produce, in addition to having a reduced weight.

Providing the walls 41, 42 at an angle with respect to each other has the advantage that the walls 41, 42 can protrude outwardly from a base of the sensor housing 10, and, thus, the light interference portion 40 is less likely to be covered with build-up such as soap, calcium, or lime deposits, which may cause inaccurate readings from the sensor 100.

Further, because the internal reflection characteristics are improved, the difference in the light detected in the cases of air and water can be made large, such that it is also possible to detect a presence of foam, in addition to detecting air and water, since the amount of light detected in the case of water is much less than the amount of light detected in the case of air.

The sensor housing 10 may be so configured that only the first wall 41, only the first and second walls 41 and 42, or the first and second walls 41, 42, and another portion of the housing 10 are transparent, while the remaining portion of the housing 10 is non-transparent. As such, the costs of manufacturing the sensor housing 10 may be reduced, as the amount of transparent material needed is reduced. For example, the walls 41, 42 may be made transparent, and may be coupled to the sensor housing 10 that is injection molded from a non-transparent material. Alternatively, the sensor housing 10 may be injection molded using two different materials. Since the walls 41, 42 protrude from the sensor housing 10, it may be easy to couple the first and second walls 41, 42 to the sensor housing 10 and may still result in excellent optical sensing since the transparent portion of the light interface portion 40 is protruded with respect to the sensor housing 10.

Alternatively, the housing 10 may be injection molded as a single piece comprised of a single material.

The sensor 100 may further comprise first and second fingers 61, 62, configured to be used for sensing turbidity of the medium external to the sensor 100. Typically, the fingers 61, 62 protrude into the medium, and transmit light from a first finger 61 toward a second finger 62. Depending on its turbidity, the medium between the fingers 61, 62 more or less attenuates the light traversing the medium, and by detecting the intensity of light entering the second finger 62 a level of turbidity of the medium can be determined.

Further sensing capabilities may be incorporated into the sensor 100 of the present disclosure. For example, the sensor 100 may comprise a temperature sensor. The temperature sensor may advantageously be disposed on a portion of the sensor housing 10 that extends into the medium external to the sensor 100, for example, one of the first and second fingers 61, 62.

The sensor 100 is configured to be installed into an appliance 1000 such as a dishwasher or washing machine, but may be adapted for installation into further configurations in which sensing of air, foam, and/or water is desirable. A controller 1100 is configured to receive a signal from the sensor 100, and may further be configured to control operation of the appliance 1000 based on the signal received from the sensor 100.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:
1. An optical sensor comprising:
   a housing having a housing interior and a light interface portion;
   a light emitting element disposed in the housing interior; and
   a light receiving element disposed in the housing interior;
   the light interface portion protruding from a base portion of the housing, the light interface portion comprising:
      a first wall disposed to receive light emitted by the light emitting element;
      a second wall disposed such that light reflected from the second wall is received by the light receiving element; and
      a cavity formed between the first and second walls
         wherein each of the first and second walls comprises a wall inner surface and a wall outer surface, wherein the outer surface of the first wall defines an optical interface between a material of the wall and a sensor-external medium and is configured such that:
            when the sensor-external medium is air, at least a portion of the light emitted by the light emitting element is totally reflected at the outer surface of the first wall and is directed from the first wall through the cavity to the second wall and from the second wall to the light receiving element; and
            when the sensor-external medium is water, at least a portion of the light emitted by the light emitting element is coupled out into the sensor-external medium at the outer surface of the first wall.

2. The optical sensor of claim 1 wherein the first and second walls are disposed at an angle with respect to each other.

3. The optical sensor of claim 2 wherein the angle between the first and second walls is within a range from 60 to 120 degrees or 70 to 110 degrees or 80 to 100 degrees.

4. The optical sensor of claim 1 wherein the wall inner surface of at least one of the first and second walls has a stepped formation.

5. The optical sensor of claim 4 wherein a height and/or width of steps of the stepped formation have a dimension that is within a range of approximately 0.4 to 1.0 millimeters.

6. The optical sensor of claim 1 further comprising first and second light guides accommodated in the housing, the first light guide disposed to direct light from the light emitting element toward the first wall, the second light guide disposed to direct light from the second wall to the light receiving element.

7. The optical sensor of claim 6 wherein the first and second light guides are disposed adjacent to the cavity formed between the first and second walls.

8. The optical sensor of claim 6 wherein at least one of the first and second light guides comprises a converging lens at an end thereof proximal to the cavity.

9. The optical sensor of claim 6 wherein at least one of the first and second light guides has an angled or curved surface portion at an end thereof remote from the cavity to direct light to a light output port of the respective light guide by total reflection.

10. The optical sensor of claim 6 wherein the first and second light guides extend in parallel with each other.

11. The optical sensor of claim 6 wherein the first and second light guides extend substantially parallel to a printed circuit board carrying the light emitting element and the light receiving element.

12. The optical sensor of claim 6 wherein the light emitting element and the light receiving element are disposed on a printed circuit board, wherein the light emitting element has a main emission axis substantially perpendicular to the printed circuit board, wherein the light receiving element has a main reception axis substantially perpendicular to the printed circuit board, wherein the first light guide is configured to divert a light ray emitted from the light emitting element in the direction of the main emission axis to a direction substantially parallel to the printed circuit board, and wherein the second light guide is configured to divert a light ray travelling in the second light guide parallel to the printed circuit board to a direction substantially parallel to the main reception axis.

13. The optical sensor of claim 6 wherein the first and second light guides are provided on a light guide support that has a portion configured to conform to at least a portion of an inner surface of the base portion of the housing.

14. The optical sensor of claim 13 wherein the light guide support further comprises a substantially cylindrical portion configured to conform to an inner surface of a substantially cylindrical portion of the sensor housing.

15. The optical sensor of claim 1 wherein a ratio of the amount of light received by the light receiving element to the light emitted by the light emitting element is less than 20% when the sensor-external medium is water, more than 80% when the sensor-external medium is air, and between 20% and 80% when the sensor-external medium comprises foam.

16. The optical sensor of claim 1 wherein a material of the first and second walls includes polypropylene.

17. The optical sensor of claim 1 wherein the wall outer surface of at least one of the first and second walls is planar.

18. An electric home appliance comprising:
   a cabinet including a wet compartment for receiving items to be washed;
   an optical sensor comprising:
      a housing having a housing interior and a light interface portion;
      a light emitting element disposed in the housing interior; and
      a light receiving element disposed in the housing interior;
      the light interface portion protruding from a base portion of the housing, the light interface portion comprising:
         a first wall disposed to receive light emitted by the light emitting element;
         a second wall disposed such that light reflected from the second wall is received by the light receiving element; and
         a cavity formed between the first and second walls wherein each of the first and second walls comprises a wall inner surface and a wall outer surface, wherein the outer surface of the first wall defines an optical interface between a material of the wall and a sensor-external medium and is configured such that:
            when the sensor-external medium is air, at least a portion of the light emitted by the light emitting element is totally reflected at the outer surface of the first wall and is directed from the first wall through the cavity to the second wall and from the second wall to the light receiving element; and
            when the sensor-external medium is water, at least a portion of the light emitted by the light emitting element is coupled out into the sensor-external medium at the outer surface of the first wall;
      wherein the optical sensor is mounted in the cabinet to protrude with the first and second walls into the wet compartment; and
   a control unit configured to receive a measurement signal based on light received by the light receiving element and control an operation of the appliance based on the measurement signal.

* * * * *